(12) United States Patent
Jones

(10) Patent No.: US 7,640,032 B2
(45) Date of Patent: *Dec. 29, 2009

(54) SYSTEMS, DEVICES AND METHODS FOR PROVIDING A REWARD BASED UPON USE OF A MOBILE COMMUNICATIONS DEVICE

(75) Inventor: Donald John Jones, Cardiff, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/102,465

(22) Filed: Apr. 14, 2008

(65) Prior Publication Data

US 2008/0221925 A1     Sep. 11, 2008

Related U.S. Application Data

(63) Continuation of application No. 11/196,756, filed on Aug. 2, 2005, now Pat. No. 7,359,723.

(51) Int. Cl.
*H04W 4/00* (2009.01)
*H04M 3/00* (2006.01)

(52) U.S. Cl. .................. 455/466; 455/418; 455/419

(58) Field of Classification Search ............ 455/466, 455/418, 419
See application file for complete search history.

(56) References Cited

U.S. PATENT DOCUMENTS 6,564,047 B1   5/2003   Steele et al.

2004/0252816 A1   12/2004   Nicolas
2006/0240851 A1   10/2006   Washburn

FOREIGN PATENT DOCUMENTS

WO    0141015    6/2001
WO    0189190    11/2001
WO    0225972    3/2002

OTHER PUBLICATIONS

Yantani et al., "Musex: A System for Supporting Children's Collaborative Learning in a Museum with PDA's," Proceedings of the 2nd IEEE International Workshop on Wireless and Mobile Technologies in Education (WMTE '04), 2004. Proceedings. Mar. 23-25, 2004, pp. 109-112.

*Primary Examiner*—Barry W Taylor
(74) *Attorney, Agent, or Firm*—James T. Hagler; Robert J. O'Connell

(57) ABSTRACT

The disclosed embodiments provide systems, devices and methods for providing a reward to a user of a mobile communications device. The described embodiments, for example, may include a mobile communications device that exchanges query data and response data, with a computer system over a communications network. The computer system includes an evaluation application operable to determine a predetermined reward based on, at least in part, the received response data. The response data is received by the mobile communications device from the user in response to query data presented to the user by the mobile communications device. The predetermined reward, for example, may affect an operational characteristic of the mobile communications device on the wireless network. Also disclosed are systems, devices and methods that include an outcome application, associated with the computer system, that generates an outcome determination based on, at least in part, the response data.

21 Claims, 7 Drawing Sheets

SYSTEMS, DEVICES AND METHODS FOR PROVIDING A REWARD BASED UPON USE OF A MOBILE COMMUNICATIONS DEVICE

BACKGROUND

The disclosed embodiments relate to mobile communications devices, and more particularly, to systems, devices and methods for providing a reward based upon use of a mobile communications device.

Mobile communication devices, such as cellular telephones, pagers and hand-held personal digital assistants ("PDA's"), communicate information including at least one of voice and data over a wireless network. Mobile communication devices are being manufactured with increased competing capabilities and are becoming tantamount to personal computers. Some mobile communication devices, such as select cellular telephones, may have an installed application programming computer platform that allows software developers to create software applications that operate on the wireless communication device. So, beyond their traditional communication functionality, mobile communication devices may additionally include the general functionality typically associated with a personal computer.

Systems for providing rewards to users have utilized personal computers and other dedicated computerized devices. One drawback associated with the use of personal computers, such as a desktop computer or a laptop computer, is that they are either not mobile or they are not conveniently operated while the user is moving about. Other reward-based systems have utilized dedicated computerized devices to gather information from, or relay information to, a user. Such dedicated computerized devices, however, typically lack the functionality to make them useful to accomplish other tasks.

Therefore, it would be desirable to provide a reward system that incorporates a multi-purpose mobile communications device.

BRIEF SUMMARY

The disclosed embodiments provide a system and method for providing a reward to a user of a mobile communications device based on the response of the user to query data presented by the mobile communications device.

In one embodiment, a mobile communications device comprises an output mechanism operable to generate a user interface and query data associated with an outcome evaluation application, wherein the query data determines at least a part of the user interface. The device further includes an input mechanism for receiving response data associated with the query data, wherein the response data is further associated with a predetermined reward affecting an operational characteristic of the mobile communications device on the wireless network.

In another embodiment, a mobile communications device comprises a communications application enabling data exchange with a wireless network and at least one output device operable to generate a user interface. The device further includes at least one data repository having query data associated with at least one criterion of an evaluation application, wherein the criterion is associated with a predetermined standard, and wherein at least a portion of the user interface is definable as a function of the query data. The device further includes an input mechanism for receiving response data related to the query data, where the response data is at least partially determinative of achieving the predetermined standard, and wherein a predetermined characteristic of the response data is determinative of a predetermined reward affecting an operational characteristic of the mobile communications device on the wireless network In yet another embodiment, a mobile communications device comprises at least one output mechanism operable to generate a user interface and at least one memory mechanism for storing data including a communications application and a resident evaluation application associated with query data and response data. The communications application operable to enable data exchange with a communications network including outputting the response data to another computer system across the communications network. The resident evaluation application operable to present the query data on the user interface, wherein the query data is associated with information relating to an outcome of a study. The response data is related to the query data and is relevant to a determination of the outcome. Further, the response data is determinative of a predetermined reward operable to modify an operational characteristic of the mobile communications device on the communications network. And, the device further includes at least one input mechanism for receiving the response data.

In a further embodiment, a mobile communications device comprises a communications application enabling data exchange with a wireless network and a device-specific identification number associated with an operational account having account characteristics affecting operation of the mobile communications device on the wireless network. The device further includes an output device operable to generate a user interface and query data received from an outcome evaluation application on another computer system across the wireless network, wherein the query data determines at least a part of the user interface. Additionally, the device includes an input device for receiving response data associated with the query data. The response data includes the device-specific identification number and is further determinable of a predetermined reward generatable by the other computer system across the wireless network. The predetermined reward effective to modify the account characteristics and is associated with the operational account based on the device-specific identification number.

In yet another embodiment, a mobile communications device comprises a communications application enabling data exchange with a wireless network and an output device operable to generate a user interface. The device further includes query data having a time-based response criterion and associated with an outcome evaluation application, wherein the query data determines at least a part of the user interface. The device also includes an input device for receiving response data having an associated response time and further associated with the query data. The response time is comparable with the time-based response criterion to determine a reward affecting an operational characteristic of the mobile communications device on the wireless network.

In still another embodiment, a system for determining a reward based upon usage of a mobile communications device comprises a communications interface enabling data exchange with a communications network. The communications interface is operable to receive response data transmitted over the communications network from a mobile electronic device. The device further includes an evaluation application operable to transmit query data across the communications network to the mobile communications device, wherein the query data prompts the user of the mobile communications device to input the response data into the mobile communications device. The mobile communications device also includes a reward application operable to identify a reward based on the response data, wherein the reward is effective to modify an operational characteristic of the mobile communications device on the communications network.

In another embodiment, an evaluation system comprises a communications interface enabling data exchange with at least one predetermined communications network, wherein the communications interface is operable to receive response data transmitted over the communications network from a mobile electronic device. The system further includes an evaluation application operable to determine at least one outcome based on a comparison of the response data to a predetermined standard. Additionally, the system includes a reward application operable to identify a reward based on the response data, wherein the reward is effective to modify an operational characteristic of the mobile communications device on the communications network.

In still another embodiment, a method of providing, a reward comprises receiving response data from a mobile communications device across, at least in part, a wireless network, where the response data corresponds to a user input associated with query data presented to the user by the mobile communications device. The method further includes determining a predetermined reward based on characteristics of the response data, where the predetermined reward affects an operational characteristic of the mobile communications device on the wireless network. Additionally, the method includes associating the predetermined reward with the mobile communications device. Computer readable medium embodiments of the above-described method are also provided.

In yet another embodiment, a method of conducting an evaluation comprises configuring a computer system on a communications network with an evaluation application, where the evaluation application generates an outcome determination that comprises a decision relating to at least one criterion of the evaluation. The method also includes receiving response data sent from a mobile communications device over at least a wireless network portion of the communications network, where the response data comprises an input into the mobile communications device by a user of the mobile communications device in response to query data presented to the user by the mobile communications device, and where the query data is associated with the criterion of the evaluation. Additionally, the method includes generating the outcome determination based on the received response data.

In another embodiment, a system for modifying performance of a wireless device comprises a user account controlling at least one operational characteristic of a mobile communications device on a communications network. The user account includes predetermined account parameters mat define the operational characteristic, and the user account is modifiable by a predetermined reward receivable across the communications network from a computer system having an evaluation application. The predetermined reward is based on response data from a mobile communications device received by the computer system over the communications network, where the response data corresponds to a user input associated with query data presented to the user through a resident evaluation application on the mobile communications device.

In yet another embodiment, a method of modifying a user account associated with a mobile communications device comprises receiving response data from a mobile communications device over a wireless network portion of a communications network. The response data corresponds to a user input associated with query data presented to the user through a resident evaluation application on the mobile communications device, where the mobile communications device is associated with the user account, and where the user account authorizes operation of the mobile communications device on at least the wireless network portion. The method also includes generating a predetermined reward based on the response data, where the predetermined reward affects an operational characteristic of the mobile communications device on the wireless network. Additionally, the method includes initiating the application of the predetermined award to the user account to modify an operational characteristic of the mobile communications device on the wireless network.

In a further embodiment, a mobile communications device in selective communication with other computer devices across at least a wireless network portion of a communications network includes a computer platform. The device further includes at feast one resident evaluation application loaded on the computer platform thereof which causes the selective presentation of query data to a user, and which is operable to cause the selective transmission of response data to another computer device on the communications network. The response data corresponds to an input into the mobile communications device by the user in reply to the query data.

In another embodiment, a method of earning a reward comprises receiving query data from across a wireless network, where the query data corresponds to at least one of an evaluation application, a reward application and an outcome application. The method further includes receiving response data corresponding to the query data, where the response data associated with a predetermined reward based on characteristics of the response data. The predetermined reward affects an operational characteristic of the mobile communications device on the wireless network. Additionally, the method includes transmitting the response data to a computer system across the wireless network. Computer readable medium embodiments of the above-described method are also provided.

In still another embodiment, a mobile communications device comprises a means for receiving query data from across the wireless network, where the query data corresponds to at least one of an evaluation application, a reward application and an outcome application. The device further includes a means for receiving response data corresponding to the query data, the response data associated with a predetermined reward based on characteristics of the response data, where the predetermined reward affects an operational characteristic of the mobile communications device on the wireless network. Additionally, the device includes a means for transmitting the response data to a computer system across the wireless network.

In yet another embodiment, a computer system comprises a means for receiving response data from a mobile communications device across a wireless network. The response data corresponds to a user input associated with query data presented to a user by the mobile communications device. The computer system also includes a means for determining a predetermined reward based on characteristics of the response data, where the predetermined reward affects an operational characteristic of the mobile communications device on the wireless network. Additionally, the computer system includes a means for associating the predetermined reward with the mobile communications device.

Additional aspects and advantages of the disclosed embodiments are set forth in part in the description which follows, and in part are obvious from the description, or may be learned by practice of the disclosed embodiments. The aspects and advantages of the disclosed embodiments may also be realized and attained by the means of the instrumentalities and combinations particularly pointed out in the appended claims.

BRIEF DESCRIPTION OF THE DRAWINGS

The disclosed embodiments will hereinafter be described in conjunction with the appended drawings provided to illustrate and not to limit the disclosed embodiments, wherein like designations denote like elements, and in which.

DETAILED DESCRIPTION

The disclosed embodiments include systems, devices and methods for providing a reward to a user of a mobile communications device based on inputs by the user into the mobile communications device. For example, in one embodiment, the user-supplied inputs may relate to clinically-important information associated with a medical clinical trial in which the user is a participant, where the reward provides an incentive for the user to provide the clinically-important information in a timely manner. Further, the disclosed embodiments include systems, devices and methods for analyzing the user-supplied inputs in order to determine an outcome based on the inputs. For example, in one embodiment, the user-supplied inputs may relate to clinically-important information associated with a medical clinical trial in which the user is a participant, where the outcome may relate to achievement of a predetermined criterion associated with the clinical trial.

Figure 1:
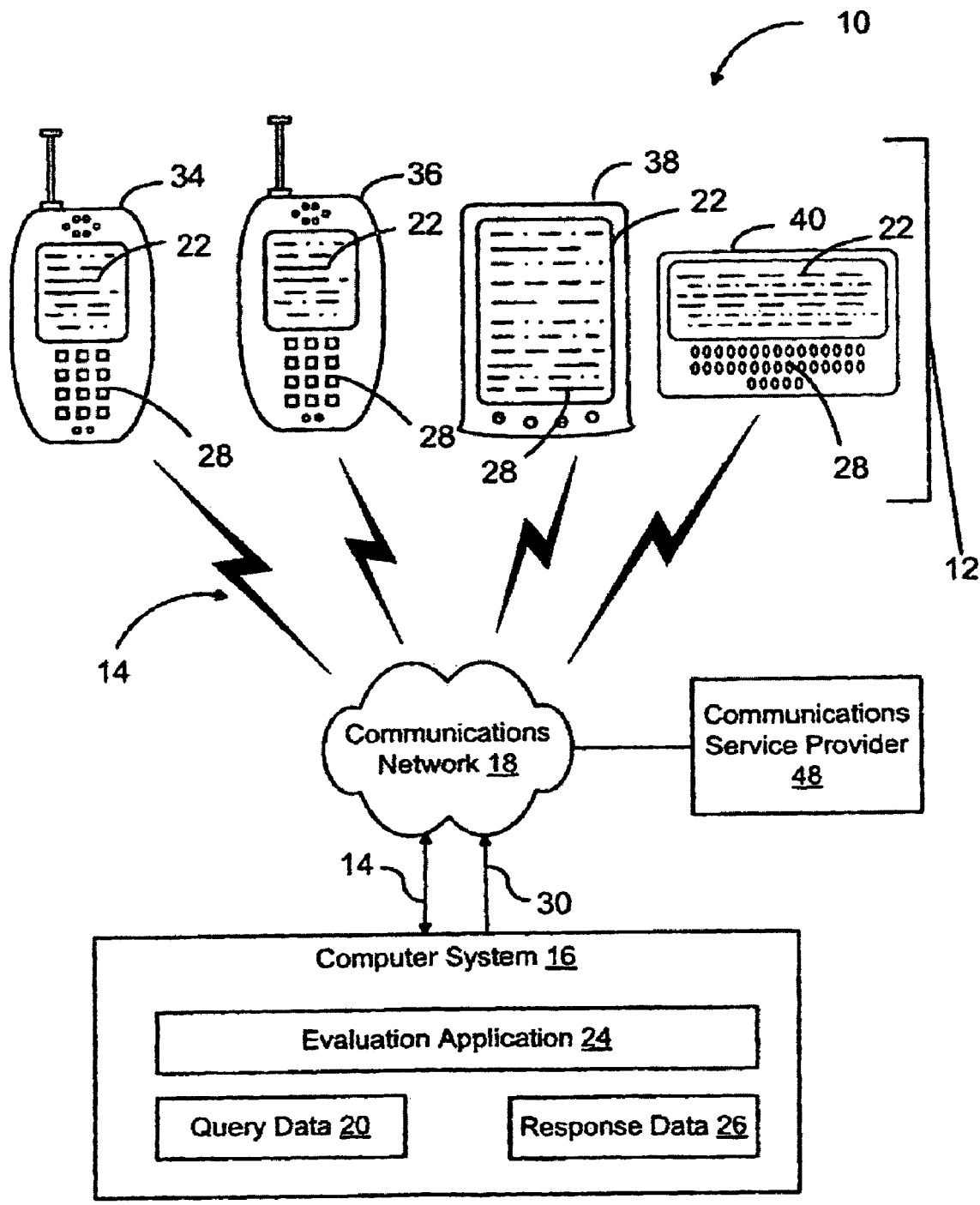
FIG. 1 is a schematic diagram of one embodiment of a reward system including mobile communications devices communicating with an evaluation application over a communications network.

Referring to FIG. 1, in one embodiment, a system 10 for providing a reward to a user includes at least one mobile communications device 12 that wirelessly exchanges communications data 14 with a computer system 16 across a communications network 18. Communications data 14 includes query data 20 presented to the user on a user interface 22, such as a display, of mobile communications device 12. An evaluation application 24 associated with computer system 16 may direct the sending of query data 20 from computer system 16 to mobile communications device 12. Additionally, communications data 14 includes response data 26 associated with query data 20 and received from the user through an input mechanism 28, such as a keypad, on mobile communications device 12. Mobile communications device 12 forwards response data 26 to computer system 16. Further, evaluation application 24 may direct an analysis of the received response data 26 resulting in a determination of a predetermined reward 30 assignable to the user based on the content and characteristics of response data 26. In one embodiment, for example, predetermined reward 30 may be a reward that affects an operating characteristic associated with mobile communications device 12. Some non-limiting examples of such an operating characteristic may be an available time of use of device 12 on communications network 18 and/or a functionality of device 12, such as a game that may be downloaded to and operated by the device. It should be noted, however, that predetermined reward 30 is not limited to any particular type of operating characteristic, and may further encompass any type of good and/or service that may be associated with mobile communications device 12 and/or its user. As such, predetermined reward 30 provides an incentive to the user of mobile communications device 12 to respond to query data 20. Because mobile communications device 12 may be a highly portable and easily operable device, even when the user is moving about, the user may consistently carry and conveniently operate device 12 to provide response data 26 in a timely manner. Thus, through mobile communications device 12, system 10 provides a user with a convenient and efficient multi-purpose tool for use in participating in a reward-based program associated with evaluation application 24.

Figure 2:
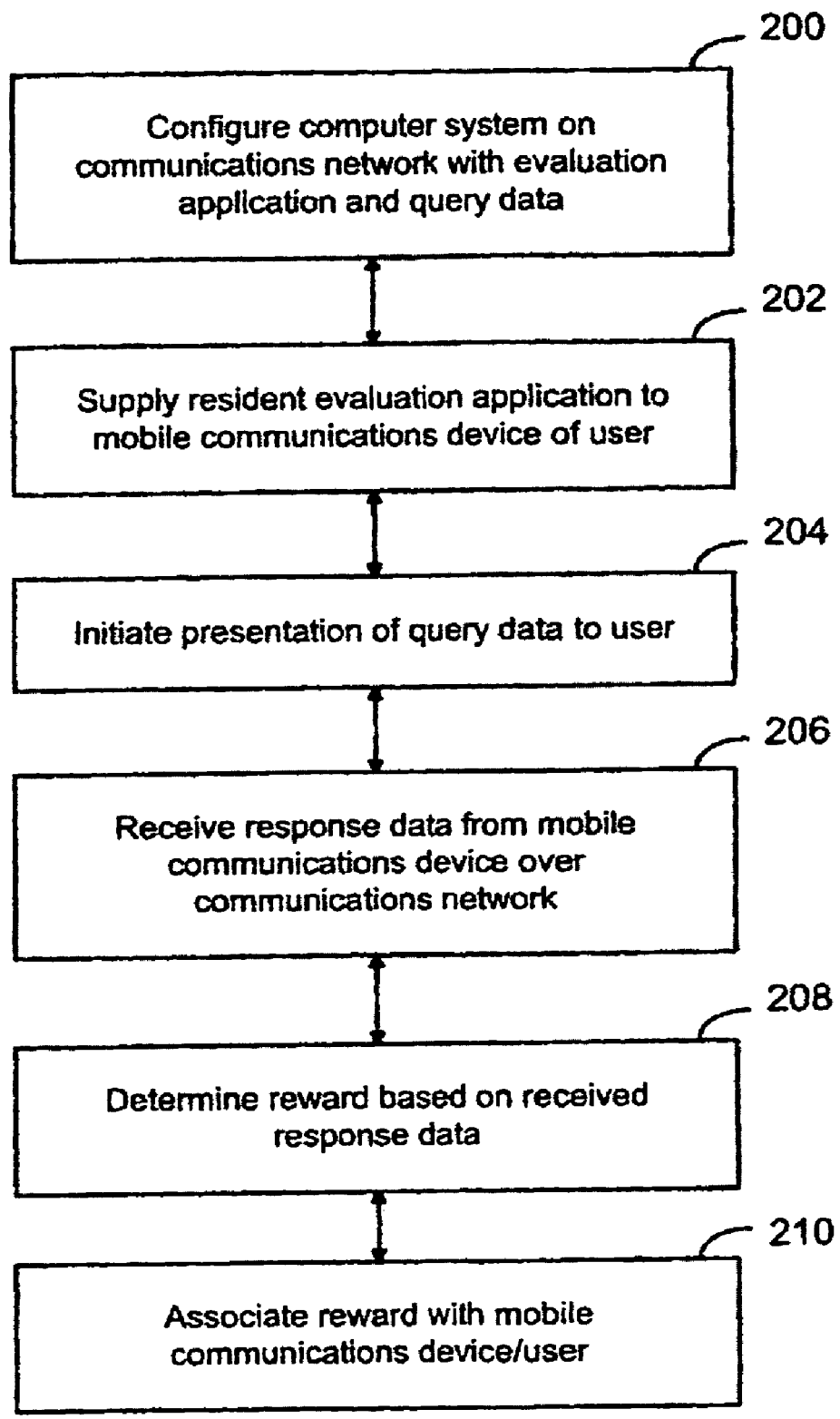
FIG. 2 is a flow chart illustrating one embodiment of a method of providing a reward to a user of a mobile communications device.

Referring to FIG. 2, in one non-limiting embodiment of a method for providing a reward, for example, the user of mobile communications device 12 is a participant in a medical clinical trial. Computer system 16 and evaluation application 24 are configured, for example, with query data 20 designed to encourage retrieval of clinically-relevant information associated with the trial from the user (Block 200). For example, as a clinical trial participant, the user may be required to take certain medications and to answer certain questions, such as regarding their physical condition, at predetermined times. To enable the user to provide this feedback to computer system 16 in exchange for predetermined reward 30, the user may be supplied with resident evaluation application 32 (Block 202). Resident evaluation application 32 works in conjunction with evaluation application 24 to direct the presentation of query data 20, and to direct the collection of response data 26 on mobile communications device 12 and the forwarding of response data 26 to computer system 20. For example, the user may be supplied with mobile communications device 12 loaded with a resident evaluation application 32. Alternatively, computer system 16 can selectively download resident evaluation application 32 and/or query data 20 across communications network 16 to a selected mobile communications device 12 operated by the user/trial participant. Based on predetermined settings within resident evaluation application 32, such as preset time periods, or based on a request by evaluation application 24 or a receipt of query data 20, mobile communications device 12 under the direction of resident evaluation application 32 can present query data 20 in the form of questions to the user/trial participant (Block 204), and transmit response data 26 in the form of answers from the user/trial participant. Such questions may be presented as output to the user by mobile communications device 12, where the output is some form of communication that includes query data 20. The user may respond to the questions, such as by providing an input to mobile communications device 12, where the input is represented as response data 26. Resident evaluation application 32 may direct the forwarding of response data 26 from mobile communications device 12 to computer system 16 across communications network 18. Computer system 16 receives response data 26 over communications network 18 from mobile communications (206). Thereafter, based on the receipt, content and/or other characteristics of response data 26, evaluation application 24 determines predetermined reward 30 (Block 208), which is associated with the user (Block 210). Further details of these systems and methods are described below.

Figure 3:
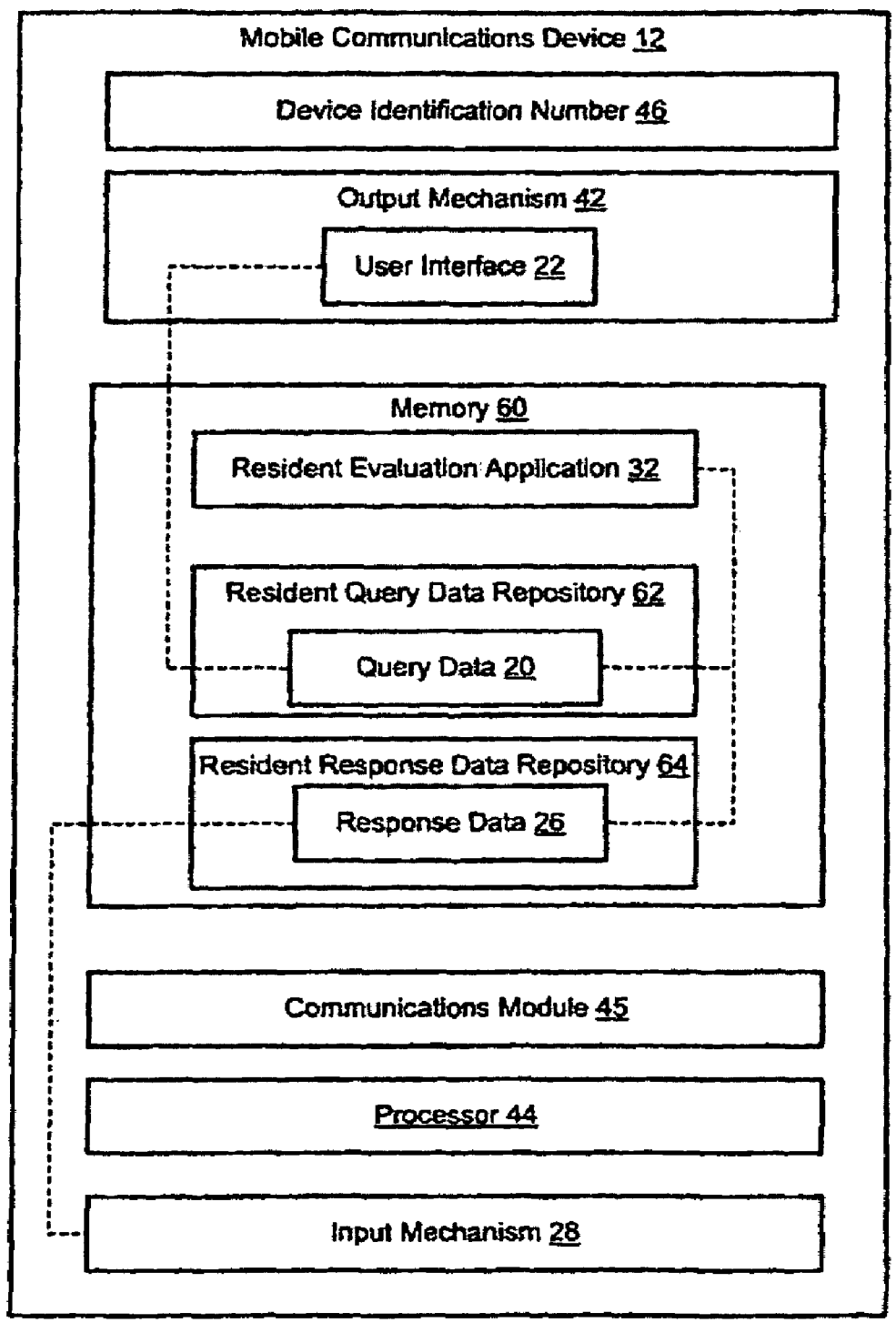
FIG. 3 is a block diagram of one embodiment of a mobile communications device associated with the system of FIG. 1.

Referring to FIGS. 1 and 3, mobile communications device 12 may include a wireless telephone, such as a cellular phone 34, a satellite phone 36, a personal digital assistant 38, a two-way pager device 40, a mobile personal computer (not shown) and any other type of portable device capable of sending and receiving communications data 14 across communications network 18. Communications data 14 may not only include query data 20 and response data 26, but also may include at least one of voice and data packets, including voice, graphical and text communications information. As such, each mobile communications device 12 may communicate to any other device associated with communications network 18. Additionally, mobile communications device 12 may have at least one output mechanism 42 controllable by a processor 44 to generate user interface 22 that, when prompted by resident evaluation application 32, includes a representation of query data 20 for soliciting a response from the user. Examples of output mechanism 42 include a display device, such as a liquid crystal display or a light-emitting diode display, an audio device such as a speaker, and a tactile device such as a rotating mechanism to create a vibration and/or a Braille character generator. Processor 44 may include at least one of a chip and a printed circuit, which extracts instructions from memory and decodes and executes them. Examples of the user interface 22 include an image or graphic, a predetermined sound, and a predetermined vibration pattern and/or a predetermined Braille character. Mobile communications device 12 may further include at least one input mechanism 28 that a user may utilize to create an input into mobile communications device 12 represented as response data 26 in association with query data 20. Examples of input mechanism 28 include a touch screen display, at least one key, an alphabetic and/or numeric keyboard, an audio input recognition device such as voice recognition software and dial tone recognition software, and any other type of device or mechanism capable of receiving an input from a user.

Additionally, mobile communications device 12 may include a communications module/application 44 having at least one of hardware, software and firmware enabling device 12 the exchange of data/instructions within device 12 and enabling the exchange of communications data 14 with communications network 18. Further, each mobile communications device 12 may include a device identification number 46 that may enable mobile communications device 12 to identify itself to a communications service provider 48 (FIG. 1). For example, device identification number 46 may be a unique identifier associated with device 12 and/or the user of device 12. Communications services provider 48, for example, may control access of mobile communications device 12 to at least a portion of communications network 18. As such, communications services provider 48 may require device identification number 46 in order to authenticate device 12 and authorize it for communications on communications network 22.

Figure 4:
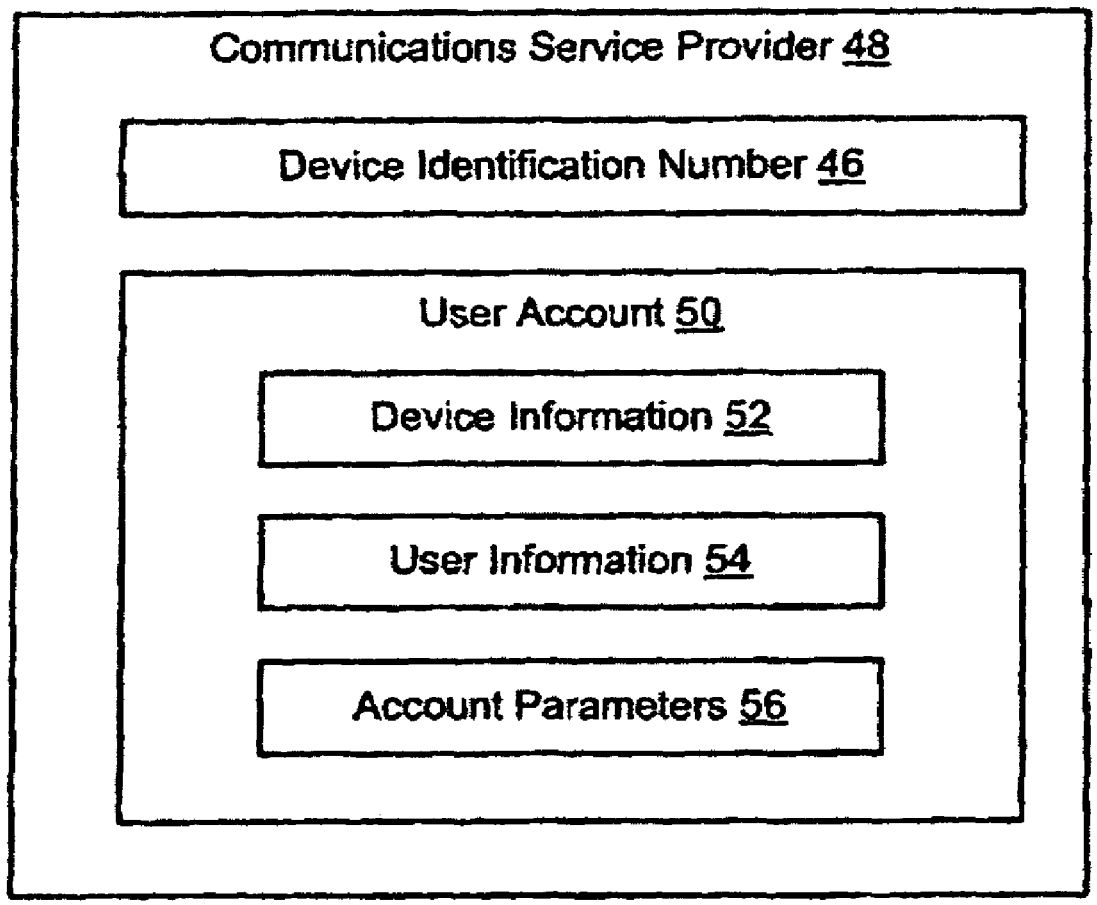
FIG. 4 is a block diagram of one embodiment of a communications service provider associated with the system of FIG. 1.

Referring, to FIG. 4, for example, one embodiment of communications services provider 48 may associate device identification number 46 to a user account 50 that defines additional device information 52, user information 54 and/or account parameters 56 associated with device 12 and/or operation of device 12 on network 18. Examples of additional device information 52 include, but are not limited to: make, model, hardware version, software version, electronic serial number, and any other unique identifier associated with the device. Examples of user information 54 include, but are not limited to: user name, user address, user telephone number, user email address, an account number associated with the user, and any other unique identifier associated with the user. Examples of account parameters include, but are not limited to: rate plan, available time of use, actual time of use, data parameters, voice parameters, multimedia parameters, and any other data associated with a characteristic of the account.

Further, referring back to FIG. 3, mobile communications device 12 has a memory 60 for storing data and/or executable instructions, such as resident evaluation application 32. Memory 60 may include at least one data repository component, such as physical or virtual memory, including at least one of read-only memory (RAM), random-access memory (ROM), programmable read-only memory (PROM), electronic programmable read-only memory (EPROM), electronically-erasable programmable read-only memory (EEPROM), flash memory, magnetic media, optical media, a soft disk, a hard disk, and any other type of secondary or tertiary memory.

Resident evaluation application 32 may be a set of executable instructions, such as a software application, stored in memory 60 of device 12 and operated by processor 44 to carry out functionality on device 12 associated with, evaluation application 24. Resident evaluation application 32 may be loaded onto device 12 at any time, such as during the initial manufacturing of device 12 and/or during a communication session between device 12 and computer system 16 across communications network 18. Resident evaluation application 32 may be in communication with a resident query repository 62, for receiving and storing query data 20, and a resident response repository 64, for receiving and storing response data 26 received from the user. In one embodiment, for example, resident evaluation application 32 may cause output mechanism 42 on mobile communications device 12 to present the user with user interface 22 that includes query data 20 from resident query data repository 90, such as in me form of a text question on a display. The user may enter an alphabetical, and/or numerical response, for example, by operating input mechanism 28, such as by depressing keys on a keypad that converts the keystrokes into an electronic format represented by response data 26. Such response data 26 may be stored in response data repository 92, and may be associated with and/or related to the corresponding query data 20. Then, at predetermined instances, resident evaluation application 32 may retrieve response data 26 from resident response data repository 92 and forward it across communications network 18 to evaluation application 24. Such predetermined instances may include, for example, upon receiving a request from evaluation application 24 and/or the user initiating a communications session on communications network 18.

Communications network 18 may include at least one or a combination of networks for providing, at least in some portion, a wireless communications transmission between two devices. Examples of communications network 18 include at least one, or any combination, of: a cellular telephone network; a satellite telephone network; an infrared network such as an Infrared Data Association (IrDA)-based network; a short-range wireless network; a Bluetooth® technology network; an ultra-wideband network ("UWB"); a ZigBee® protocol network; a home radio frequency (HomeRF) network; a shared wireless access protocol (SWAP) network; a wideband network, such as a wireless Ethernet compatibility alliance (WECA) network, a wireless fidelity alliance (Wi-Fi Alliance) network, an 802.11 network; a public switched telephone network; a public heterogeneous communications network, such as the Internet; a private communications network; and a medical network, such as a medical implant communications ("MIC") network; a telemetry network, etc.

Examples of telephone networks include at least one, or any combination, of analog and digital networks/technologies, such as: Personal Communications Services, code division multiple access, wideband code division multiple access, universal mobile telecommunications system, advanced mobile phone service, time division multiple access, frequency division multiple access, global system for mobile communication, analog and digital satellite systems, and any other technologies/protocols that may be used in at least one of a wireless communications network and a data communications network.

Referring to FIG. 4, computer system 16 may beat least one of any type of personal computer, mini-mainframes and the like. Computer system 16 includes a bus 66 or other communication mechanism for communicating information, and a processor 68 coupled with the bus 66 for processing information. Computer system 16 also includes a main memory 70, such as a random access memory (RAM) or other dynamic storage device, coupled to the bus 66 for storing communications data 14, and other data and instructions related to evaluation application 24 to be executed by processor 68. Main memory 70 also may be used for storing temporary variables or other intermediate information during execution of instructions to be executed by processor 68. Computer system 16 may further include a read only memory (ROM) 72 or other static storage device coupled to the bus 66 for storing static information and instructions for the processor 68. A storage device 74, such as a magnetic disk or optical disk, is provided and coupled to the bus 66 for storing communications data 14, and other data and instructions related to evaluation application 24.

Computer system 16 may be coupled via the bus 66 to a display 76, such as a cathode ray tube (CRT) or a flat panel display, for displaying information to a user. An input device 78 is coupled to the bus 66 for communicating information and command selections to the processor 68. For example, input device 78 may include, but is not limited to, alphanumeric keys, function keys, voice input devices, touch screen devices, sensor devices such as passive data gatherers, accelerometers, pedometers, physiological monitors, and any other type of input receiving mechanism. Another type of user input device may be a cursor control 80, such as a mouse, a trackball, or cursor direction keys for communicating direction information and command selections to processor 68 and for controlling cursor movement on the display 76. This input device typically has two degrees of freedom in two axes, a first axis (e.g., x) and a second axis (e.g., y) allowing the device to specify positions in a plane.

Figure 5:
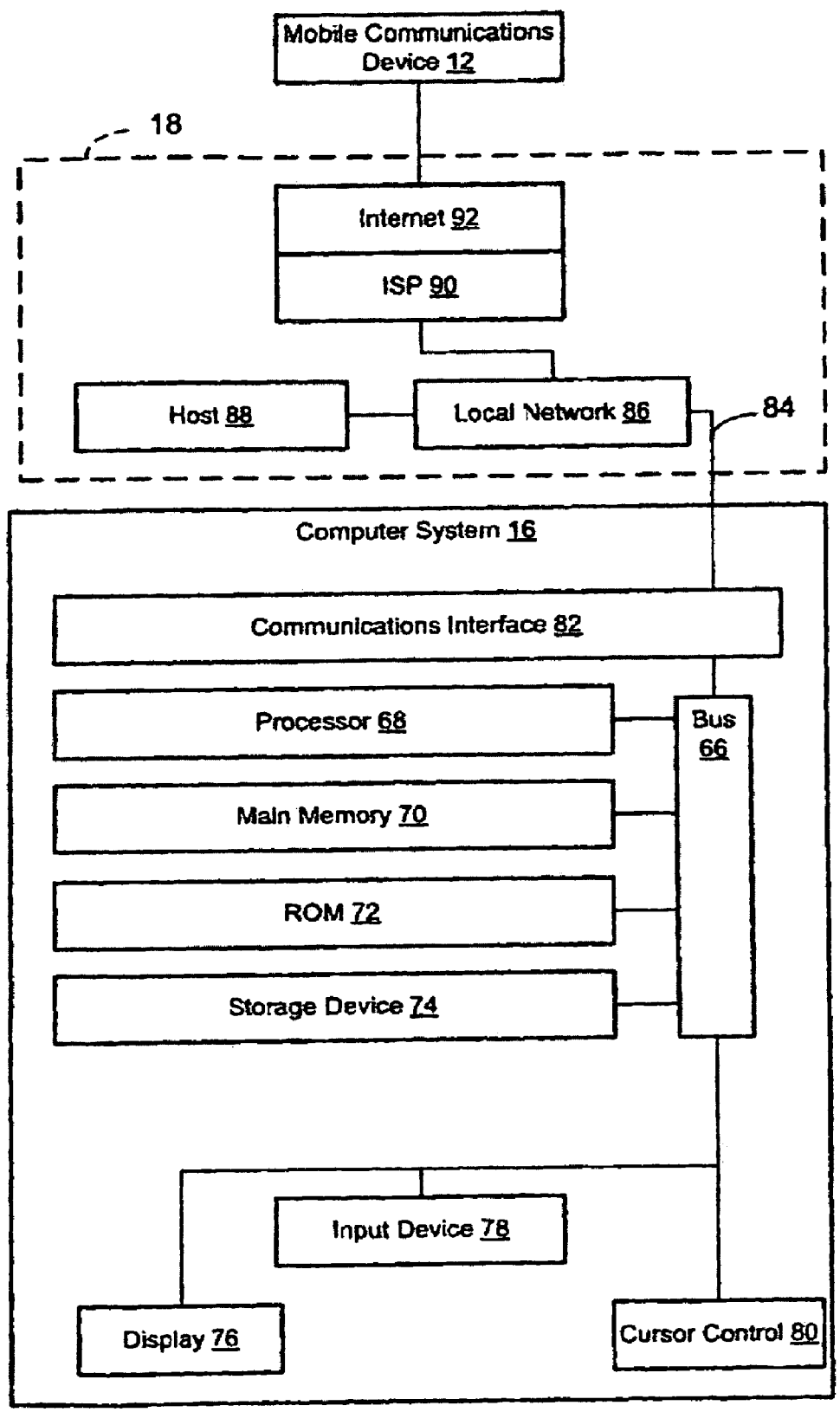
FIG. 5 is a block diagram of one embodiment of a computer system associated with the system of FIG. 1.

The described embodiments relate to the use of computer system 16, such as the embodiment of FIG. 5, to manage communications with at least one mobile electronic device 12 to carry out the instructions of evaluation application 24 to send query data 20 and collect response data 26. According to one embodiment, query data 20 and response data 26 are tracked and analyzed by computer system 16 in response to processor 68 executing sequences of instructions contained in main memory 70 in response to input received via input device 78, cursor control 80, or communication interface 82. Such instructions may be read into main memory 70 from another computer-readable medium, such as storage device 74. However, the computer-readable medium is not limited to devices such as storage device 74. For example, the computer-readable medium may include a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave embodied in an electrical, electromagnetic, infrared, or optical signal, or any other medium from which a computer can read. Execution of the sequences of instructions contained in the main memory 70 causes the processor 68 to perform the process steps described below. In alternative embodiments, hard-wired circuitry may be used in place of or in combination with computer software instructions to implement the described embodiments. Thus, the described embodiments are not limited to any specific combination of hardware circuitry and software.

Computer system 16 also includes a communication interface 82 coupled to the bus 66. Communication interface 82 provides two-way data communication with another device and/or network. For example, communication interface 82 may be an integrated services digital network (ISDN) card, a digital subscriber line (DSL) card, or a modem to provide a data communication connection to a corresponding type of telephone line. As another example, communication interface 82 maybe a local area network (LAN) card to provide a data communication connection to a compatible LAN. Wireless links may also be implemented. In any such implementation, communication interface 82 sends and receives electrical, electromagnetic or optical signals which carry digital data streams representing various types of information. Of particular note, the communications through interface 82 may permit transmission or receipt of query data 20, response data 26, predetermined reward 30 and another other data and/or instructions associated with evaluation application 24 and/or system 10. For example, two or more computer systems 16 may be networked together in a conventional manner with each using the communication interface 82.

Network link 84 typically provides data communication through one or more networks to other data devices. For example, network link 84 may provide a connection through local network 86 to a host computer 88 or to data equipment operated by an Internet Service Provider (ISP) 90. ISP 90 in turn provides data communication services through the world wide packet data communication network now commonly referred to as me "Internet" 92. Local network 86 and Internet 92 both use electrical, electromagnetic or optical signals which carry digital data streams. The signals through the various networks and the signals on network link 84 and through communication interface 82, which carry the digital data to and from computer system 16, are exemplary forms of carrier waives transporting the information. It should be noted that communications network 22 may include any combination of network link 84, local network 86, host computer 88, ISP 90 and Internet 92.

Computer system 16 can send messages, including program code, and receive data through the network(s), network link 84 and communication interface 82. In the Internet example, mobile communications device 12 might transmit a requested code for an application program through Internet 92, ISP 88, local network 86 and communication interface 82. In accordance with the described embodiments, one such downloaded application is resident evaluation application 32 that provides for the local management on device 12 of query data 20, response data 26 and other additional instructions associated with evaluation application 24.

Figure 6:
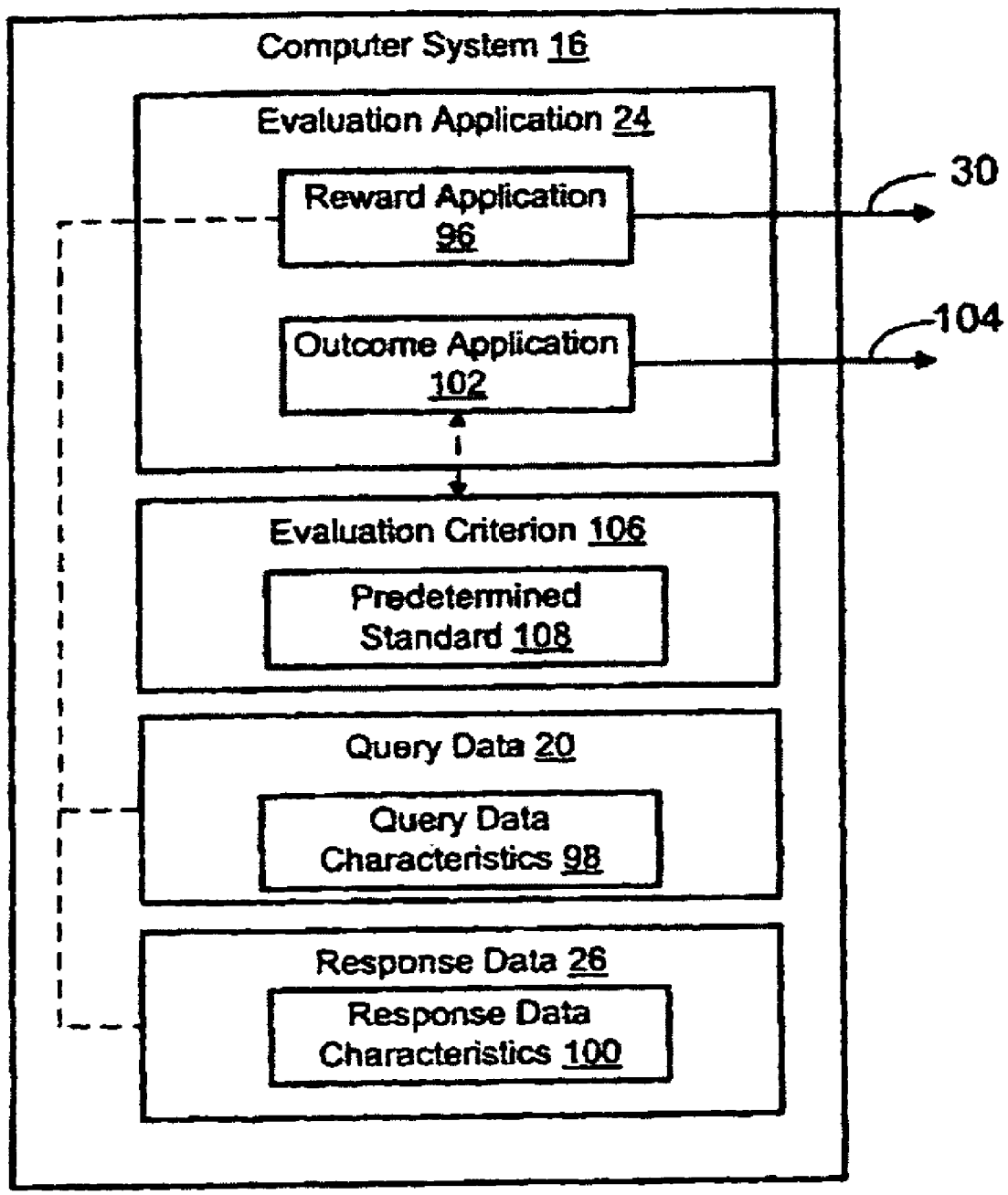
FIG. 6 is a block diagram of one embodiment of additional components of the computer system of FIG. 5.

Referring to FIGS. 1 and 6, evaluation application 24 may be a set of executable instructions, such as a software application, stored on computer system 16 and operable to generate predetermined reward 30. Evaluation application 24 may be configured to collect certain types of information from user, such as information related to: a program, a study, an evaluation, a market analysis, a poll, a test, a game, a medical clinical trial, a marketing analysis, a medical reimbursement, a reward program, a loyalty program, an achievement program, a compliance program, an advertising campaign, an educational program, a disease management program, and/or any other event in which presentation of query data 20 to the user and/or analysis of response data 26 may be useful. Further, evaluation application 24 may include a reward application 96 that includes a set of executable instructions, algorithms, tables, etc. that may be utilized to review response data 26, in association with the corresponding query data 20, to determine predetermined reward 30.

Query data 20 may be any data associated with a program, study, evaluation or any other event associated with evaluation application 24 that present information and/or assist in identifying and/or collecting data that may be utilized by evaluation application 24. For example, query data 20 may prompt a user to take an action, such as to interact with the wireless device to enter information. For instance, query data 20 may prompt a user to perform and action, such as to call a phone number, to take a medication, to enter a value corresponding to a perceived level of pain, to enter a value corresponding to a reading on a sensing device (e.g. a scale, a peakflow meter, a glucometer, blood pressure, heart rate, etc.), to enter a sample into a metering device connected to the wireless device, to answer a educational test question, to answer a multiple choice question, etc. Further, for example, response data 26 may be any data received from the user of mobile communications device 12 in response to query data 20. Further, query data 20 and response data 26 may contain or may be further associated with respective query data characteristics 98 and response data characteristics 100 that relate in some fashion to the query and response data. For instance, query data 20 may be an electronically-generated representation of information, that is presentable to the user of mobile communications device 12. For example, query data 20 may be presented in the form of text, graphics, video, audio sounds, mechanical movements or vibrations, and in any other manner to transmit information to a user. Query data characteristics 98 may include at least one of a qualitative, quantitative, subjective and objective data related to query data 20, such as: a numerical value, an alpha character or set of characters, a descriptive word, a time at which the query data was sent to the user, a time at which the query data was presented to the user, a marker or pointer that identifies other data to which the query data is related, an audio sound, a mechanical movement, etc. Similarly, response data 26 may be aft electronic representation of information that is received from the user of mobile communications device 12. For example, response data 26 may result from a mechanical input, an audio input, etc. Response data characteristics 100 may include at least one of a qualitative, quantitative, subjective and objective data related to response data 26, such as: a numerical value, an alpha character or set of characters, a descriptive word, a time at which the response data was received from the user, a time at which the response data was sent to the computer system, a marker or pointer that identifies other data to which the response data is related, an indicator of the existence of response data 26 associated with a particular query data 20, a response time representative of a difference between a time at which query data 20 was presented to the user and a time at which response data 26 was received from the user, audio data, sensor data, meter data such as from a glucose meter, physiological data parameters, distance traveled or other pedometer-related data, acceleration and/or velocity or or other accelerometer-related data, and any other parameter associated with response data 26.

Predetermined reward 30 may be used in conjunction with evaluation application 24 to encourage the participation of the user of mobile device 12 in the program, study, evaluation, etc., or any other event associated with evaluation application 24 where presentation of query data 20 to user is desired, and/or where user input is desired for analysis and/or to determine an outcome. Examples of predetermined reward 30 include, but are not limited to: no reward; a beneficial reward such as a credit; a detrimental reward such as a debit; a reward affecting an operating characteristic and/or functionality of wireless mobile communications device 12; an ability to operate a predetermined application and/or functionality on device 12; an authorization to operate device 12 on at least a portion of communications network 18, such as a wireless network portion and/or any other network portion, which may be controlled by communication services provider 40; an available time of use for operating device 12; an available time of use for operating device 12 on at least a portion of communications network 18, such as a wireless network portion and/or any other network portion, which may be controlled by communication services provider 40; an applicable cost and/or rate associated with a predetermined operating time or function of device 12, such as may be associated with operation on at least a portion of communications network 18, such as a wireless network portion and/or any other portion, which may be controlled by communication services provider 40; an ability to retrieve an award, such as a link and/or a code to use to obtain music, videos, pictures, software applications, etc.; credits for games, ring tones, entertainment, call minutes, text messaging, photo exchange, media, Internet-based awards; and any other type of reward available within communications network and/or outside of communications network.

Additionally, evaluation application 24 may further include at least one outcome application 102 that generates at least one outcome determination 104 based on, at least in part, the received response data 26 and/or one or more of response data characteristics 100, query data 20 and query data characteristics 98. Outcome application 102 may include some combination of a set of executable instructions, algorithms, tables, etc., that comprise a decision-making program able to analyze data and establish outcome determination 104. Outcome application 102 may further be associated with evaluation criterion 106, such as at least one factor associated with a determination of whether or not a particular outcome, such as at least one predetermined standard 108, has been achieved. For example, predetermined standard 108 may include at least one of a range of values or an individual value that is associated with achieving or not achieving evaluation criterion 106. Evaluation criterion 106 and predetermined standard 108 may be stored within memory 70 of computer system 16. As such, outcome determination 104 may be a decision or recommendation relating to the analysis performed by outcome application 102, and outcome determination 104 may be based, at least in part, on at least one of received response data 26 and response data characteristics 30, and their relationship to at least one of evaluation criterion 106 and predetermined standard 108.

Additionally, it should be noted that evaluation application 24, reward application 96 and/or outcome application 102 may utilize query data 20 and/or response data 26 that is associated with an individual mobile electronic device 12 for making determinations related to an individual user, as well as a predetermined grouping of a plurality of mobile communications devices to make determinations about a group of users.

For example, as discussed above, a clinical trial for a drug or medical device may involve registering qualified participants, administering the drug at predetermined times or installing the predetermined medical device, and collecting qualitative, quantitative, subjective and/or objective feedback associated with predetermined criteria at predetermined times. For instance, the feedback may include details relating to how well the participant feels at a given time, how well the participant feels the drug is working, test results or objective measurements that form a factual basis as to how well the drug is working, etc. This, feedback is prompted by query data 20 presented on wireless mobile communications device 12, and then the input into the device is relayed over communications network 18 to evaluation application 24. Evaluation application 24 and/or outcome application 102 then analyze response data 26. For example, this analysis may involve comparing the received data wife known standards and determining whether or not the data meets these predetermined standards. Based on this analysis, evaluation application 24 then generates at least one of predetermined reward 30 and outcome determination 104. Predetermined reward 30 may affect the user of wireless mobile device 12 by affecting an operating characteristic of device 12, such as, in one embodiment where device 12 is a cellular telephone, by adding free minutes to the user account of the cellular telephone.

Other examples of evaluation application 24, reward application 96 and/or outcome application 102 include education programs, learning or skills training/testing programs, diabetes testing programs, monitoring programs such as behavior or health management programs, surgery preparation and recovery programs, etc.

In one non-limiting embodiment, these programs may effectively manage the minutes on a phone plan associated with the respective mobile communications device 12 For example, upon signing up to participate in using one of evaluation application 24, reward application 96 and/or outcome application 102, the user of mobile communications device 12 may have a predetermined number of available minutes assigned to an account associated with the mobile communications device. Applications 24, 96 and/or 102 may then operate to provide the user with additional available minutes, or limit access to a subset of the predetermined number of available minutes, depending upon the received response data 26, e.g. depending on if the user completes a survey.

Advantageously, the present system allows any party, such as a sponsor of evaluation application 24, reward application 96 and/or outcome application 102, to purchase and associate/apply reward 30 to mobile communications device 12. This feature allows the present system to present query data, collect response data, and manage the respective application essentially without the user of mobile communications device 12 having any interaction with a carrier network or network services provider, i.e. the provider of the network on which device 12 operates. Thus, the present system operates in a transparent manner with respect to both the user and the carrier network or network services provider.

Figure 7:
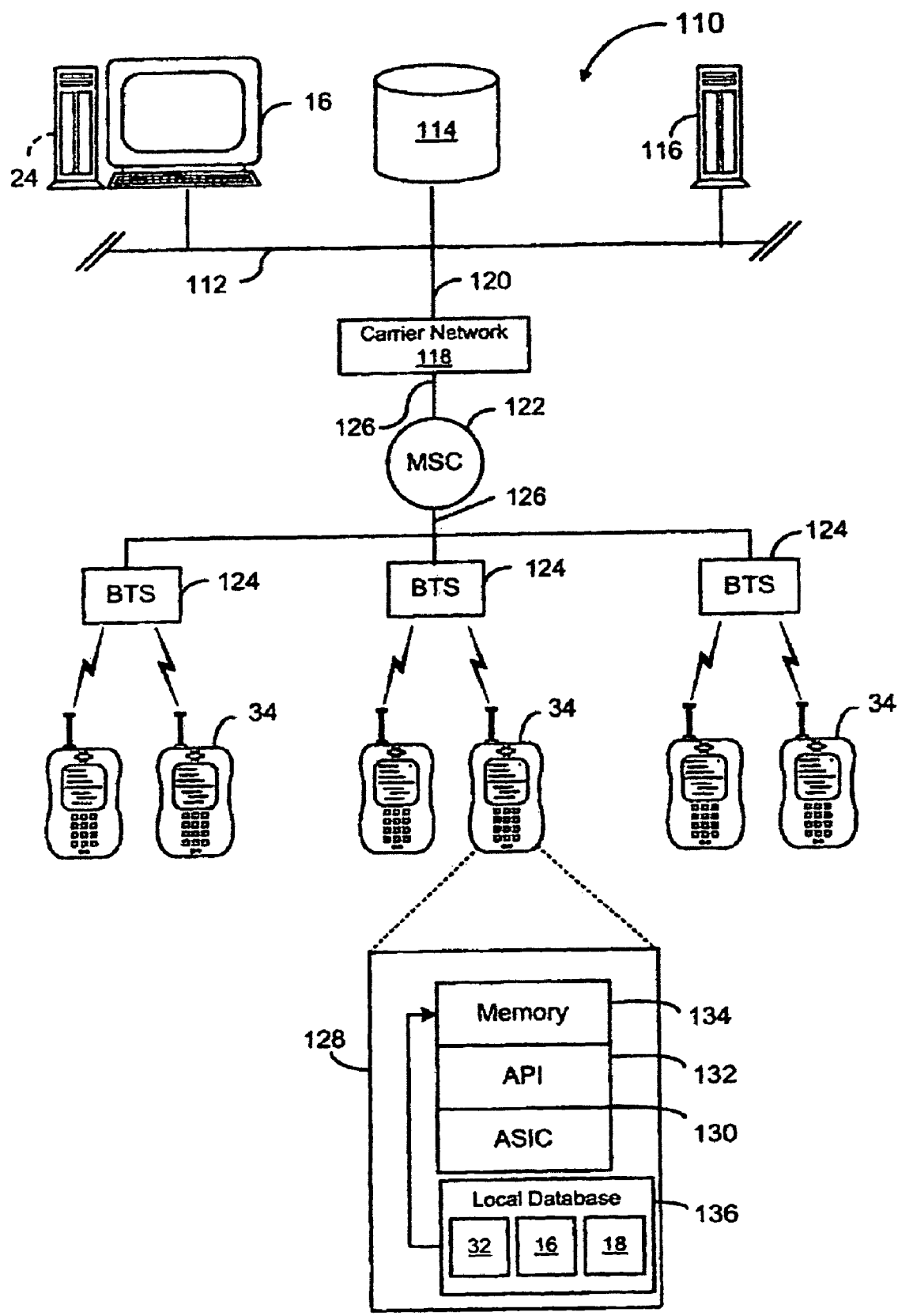
FIG. 7 is a schematic diagram of a wireless network associated with the system of FIG. 1.

In another embodiment, referring to FIG. 7 for example, system 10 (FIG. 1) may include a cellular telephone network 110. The use of cellular telecommunication pathways has been increasing because wireless mobile communications devices 12 (FIG. 1), such as cellular telephone 34, are being manufactured with increased computing capabilities and are becoming tantamount to personal computers, communicating packets including at least one of voice and data over the wireless network. Embodiments of these "smart" cellular telephones, for example, have installed application programming interfaces ("APIs") onto their resident computer platform that allow software developers to create software applications that operate on the cellular telephone, and control certain functionality on the device. FIG. 7 is a block diagram that more fully illustrates the components of a cellular wireless network and interrelation of the elements of the present system. Cellular telephone network 110 is merely exemplary and can include any system whereby remote modules, such as cellular telephones 34, communicate over-the-air between and among each other and/or between and among components of a cellular telephone network 110, including, without limitation, wireless network carriers and/or servers.

Still referring to the embodiment of FIG. 7, computer system 16 and evaluation application 24 may be present on the cellular telephone network 110 with any other components that are needed to provide cellular telecommunication services. For example, computer system 16 may operate on LAN 112 with additional data repository 114 and/Or an additional data management or post-processing server 116. Computer system 16 communicates with a carrier network 118 through a data link 120, such as the Internet, a secure LAN, WAN, or other network. Carrier network 118 controls messages (generally being data packets) sent to a messaging service controller ("MSC") 122. Carrier network 118 communicates with the MSC 122 through another communications link 123, such as another network, the Internet, and/or POTS ("plain ordinary telephone system"). Typically, the network or Internet connection between carrier network 118 and the MSC 122 transfers data, and the POTS transfers voice information. The MSC 122 may be connected to multiple base stations ("BTS") 124, such as by at least one communications link 126, including both a data network and/or the Internet for data transfer and POTS for voice information. BTS 124 ultimately broadcasts messages wirelessly to the mobile communications devices, such as cellular telephones 34, in an over-the-air protocol such as short messaging service ("SMS"), etc.

In the embodiment of FIG. 7, each wireless device, such as cellular telephone 44, may include a computer platform 128 that can receive and execute software applications and display data transmitted from computer system 16 or other network servers 116. Computer platform 128 may include an application-specific integrated circuit ("ASIC") 130, or other chipset, processor, microprocessor, logic circuit, or other data processing device. ASIC 130 may be installed at the time of manufacture of the wireless mobile communications device 34. ASIC 130 or other processor may execute an application programming interface ("API") layer 132 that interfaces with any resident programs in the memory 134 of the wireless device. Memory 134, for example, can be comprised of at least one of read-only and random-access memory (RAM and ROM), EPROM, EEPROM, flash cards, and any memory common to computer platforms. The computer platform 128 may also include a local database 136 that can hold the software applications, file, or data not actively used in memory 134, such as resident evaluation application 32, query data 20 downloaded from computer system 16 and response data 26 received from the user of cellular telephone 34. Local database 136 may include at least one of flash memory cells, magnetic media, EPROM, EEPROM, optical media, tape, a soft disk, a hard disk, and any other type of secondary or tertiary memory. Thus, in the embodiment of FIG. 7, each cellular telephone 34 may be loaded with resident evaluation application 32 and/or query data 20 and operable to present query data 20 to the user and collect the corresponding response data 26, and forward the response data 26 across wireless network 110, which may form at least a portion of communication network 18 (FIG. 1), to evaluation application 24, which assigns predetermined reward 30.

Thus, mobile communications device 12, which can be a part of the system or separate thereto, may have at least one resident evaluation application (either permanent or temporarily) 32 on the computer platform 128 thereof which causes the selective transmission of query data 20 and/or response data 26 for that device to another computer device (such as computer system 16) on communications network 18. If device 12 is so embodied, query data 20 and/or response data 26 is transmitted over an open communications connection from the wireless device 12 to communications network 18, such as an open voice or data call. If device 12 is a cellular telephone 34 and communications network 18 includes a cellular telecommunication network, such as shown in FIG. 7, then query data 20 and/or response data 26 can be transmitted through short message service.

In view of the method being executable on the computer platforms of a device 12, and on computer system 16, embodiments of the system can be implemented with at least one program resident in a computer readable medium, where the program directs a device 12 and/or computer system 16 to perform the steps of the method. Such a program can be executed on any single computer platform, or can be multithreaded among several computer platforms. Furthermore, embodiments include a program that directs a computer device such as computer system 16 to perform the steps of generating predetermined reward 30 and/or outcome determination 104 through gathering and processing response data 26 from the at least one wireless device 12.

For example, the computer readable medium can be memory 134 of computer platform 128 of cellular telephone 34, memory 60 associated with mobile communications device 12, and/or memory 70 associated with computer system 16. Such memory can be in a local database, such as local database 136 of the device platform 64 and/or in another database such as data repository 114. Further, the computer readable medium can be in a secondary storage media that is loadable onto a wireless device computer platform, such as a magnetic disk or tape, optical disk, hard disk, flash memory, or other type of storage media.

Further, the method embodiments may be implemented, for example, by operating portion(s) of system 10 and/or network 110 to execute a sequence of machine-readable instructions. The instructions can reside in various types of signal-bearing or data storage primary, secondary, or tertiary media. The media may comprise, for example, RAM (not shown) accessible by, or residing within, the components of system 10 and/or network 110. Whether contained in RAM, a diskette, or other secondary storage media, the instructions may be stored on a variety of machine-readable data storage media, such as DASD storage (e.g., a conventional "hard drive" or a RAID array), magnetic tape, electronic read-only memory (e.g., ROM, EPROM, or EEPROM), flash memory cards, an optical storage device (e.g. CD-ROM, WORM, DVD, digital optical tape), paper "punch" cards, or other suitable data storage media including digital and analog transmission media.

While the various disclosed embodiments have been illustrated and described, it will be clear that the subject matter of this document is not limited to these embodiments only. Numerous modifications, changes, variations, substitutions and equivalents will be apparent to those skilled in the art without departing from the spirit and scope of the disclosed embodiments as described in the claims. Furthermore, although elements of the described embodiments may be described or claimed in the singular, the plural is also contemplated.

What is claimed is:

1. A computer system to communication with a mobile communication device, the computer system comprising:
    a communication interface adapted to transmit query data to the mobile communication device and adapted to receive response data from the mobile communication device over a network;
    a processor having an evaluation application coupled to the communication interface; and
    a memory coupled to the processor, the memory containing predefined criteria, wherein the evaluation application is adapted to compare the response data received by the communication to predefined criteria, such that
    the evaluation application is adapted to provide a reward based on the comparison of the response data to the predefined criteria.

2. The computer system of claim 1 wherein the processor causes the reward to be transmitted to a communications service provider.

3. The computer system of claim 1 wherein the evaluation application is adapted to provide one of a plurality of rewards based on the comparison of the response data to the predefined criteria.

4. The computer system of claim 3 wherein the plurality of rewards comprises a series of graduated rewards.

5. The computer system of claim 1 wherein the processor is adapted to download a resident evaluation application to a mobile communication device such that the resident evaluation application causes the query data to be displayed on the mobile communication device.

6. The computer system of claim 1 wherein the predefined criteria is selected from a group of criteria consisting of one or more of: how well a participant feels; how well a participant feels a product is working, or test results.

7. The computer system of claim 1 wherein the predefined criteria comprises evaluating the response data over time.

8. A mobile communications device, comprising:
    a communications module adapted to transmit and receive data over a communication network;
    a processor to run a resident evaluation application;
    a display, the resident evaluation application in response to query data adapted to cause the display to display the query data to a user; and
    an input adapted to allow a user to input response data in response to the query data displayed on the display; such that
    the resident evaluation application is adapted to transmit the response data over the communication network to an evaluation application that compares the response data to a predefined criteria to determine one of a plurality of rewards for providing the response data.

9. The mobile communications device of claim 8 wherein the resident evaluation application is downloaded over the communication network.

10. The mobile communication device of claim 8 wherein the mobile communication device is selected from the group of communication devices consisting of: a cellular telephone, a satellite telephone, a personal digital assistant, a pager, or a mobile personal computer.

11. The mobile communications device of claim 8 wherein the resident application causes the query data to be displayed to solicit response data selected from a group of response data consisting of: how well a participant feels; how well a participant feels a product is working, or test results.

12. A system for evaluating the effectiveness of medical product or drug that facilitates participation by providing a reward based on response data, comprising:

transmitting query data to a mobile communications device relating to the medical product or drug;

receiving response data from the mobile communications device, the response data corresponding to the query data and adapted to be compared to a predefined criteria;

comparing the response data received from the mobile device to the predefined criteria;

determining a reward based on the comparison of the response data received from the mobile communications device to the predefined criteria; and awarding the reward.

13. The system for evaluating of claim 12, comprising establishing the predefined criteria.

14. The system for evaluating of claim 12 wherein transmitted query data is designed to solicit the response data selected from a group of response data consisting of: how well a participant feels; how well a participant feels a product is working, or test results.

15. The system for evaluating of claim 12, comprising downloading a resident evaluation application to the mobile communications device, the resident evaluation application adapted to cause the query data to be displayed on a display of the mobile communications device.

16. The system for evaluating of claim 12, wherein the determining the reward comprises selecting one of a plurality of rewards.

17. The system for evaluating of claim 16, wherein the plurality of rewards are graduated rewards.

18. The system for evaluation of claim 12, wherein awarding the reward comprises updating a user account with the reward.

19. A computer system in selective communication with at least one mobile communications device, comprising:

means for transmitting and receiving data over a communication network, the means for transmitting adapted to transmit query data to the mobile communications device, the means for receiving data adapted to receiver response data transmitted from the mobile communications device in response to the query data;

means for evaluating the response data against a predefined criteria; and means for awarding a reward wherein the reward is based on the means for evaluating the response data against the predefined criteria.

20. The computer system of claim 19 wherein the predefined criteria data is designed to solicit response data selected from a group of response data consisting of: how well a participant feels; how well a participant feels a product is working, or test results.

21. Computer readable code encoded on a computer readable medium that when executed, directs a computer system in communication with a communication network to perform the acts of:

transmitting at least one query data to a communication network to be received by a communication device;

receiving at least one response data from the communication network transmitted by a communication device relating to the at least one query data;

evaluating the at least one response data from the communication network to at least one predefined criteria relating to performance of a medical product, drug, or procedure; and awarding a reward based on the evaluation of the at least one response data from the communication network to at least one predefined criteria.

* * * * *